United States Patent [19]

Vasseur

[11] 3,937,965
[45] Feb. 10, 1976

[54] RADIOGRAPHY APPARATUS

[75] Inventor: Jean Pierre Vasseur, Paris, France

[73] Assignee: Thomson-CSF, Paris, France

[22] Filed: Oct. 29, 1974

[21] Appl. No.: 518,889

[30] Foreign Application Priority Data

Oct. 30, 1973  France .............................. 73.38641

[52] U.S. Cl. ................. 250/366; 250/505; 250/514
[51] Int. Cl.².... G01T 1/20; G02B 5/00; G21K 1/02
[58] Field of Search ............ 250/402, 505, 514, 366

[56] References Cited
UNITED STATES PATENTS 2,946,889   7/1960   Muench .............................. 250/366
2,992,331   7/1961   Bonner et al. ...................... 250/366

Primary Examiner—James W. Lawrence
Assistant Examiner—T. N. Grigsby
Attorney, Agent, or Firm—Cushman, Darby & Cushman

[57] ABSTRACT

A novel apparatus for radiographic examination purposes comprises an x-ray source emitting a flat beam. Detectors are arranged in the plane of the beam in order each to pick up part of the beam. To avoid the Compton effect, each detector is associated with it an auxiliary detector which only receives the rays emitted by the Compton effect. An electrical circuit forms a predetermined linear combination of the signals respectively picked up by each detector and the associated auxiliary detector, this in order to prevent the errors which are due to the Compton effect when beam passes through the body being analysed.

8 Claims, 8 Drawing Figures

RADIOGRAPHY APPARATUS

The present invention relates to a novel radiography apparatus.

In the known apparatus of this kind, an X-ray emission device is employed which illuminates a given volume of the body being examined. The image produced upon the display screen (and the resultant photograph), tends to be blurred because of the following reasons:

For one thing the volume is viewed on a flat surface, and for another the diffusion effect known as the Compton effect, increases the blurring still further.

To improve the definition of the images thus obtained, it is known to use an X-ray source emitting a very fine beam and a detector is connected to the source in order to receive the beam whatever the position of the system. Parallel plane sections of the body are scanned in succession by the source-detector system. The analysis thus made makes it possible, with help of a data-processing system, to achieve a very fine analysis of the volume. It is clear, however, that the analysis takes quite a long time, scanning of the body in effect being a two-dimensional process; moreover, the Compton effect is only of second order.

In order to reduce the analysis time, it has been proposed that a source should be used which emits a beam which is concentrated in a plane. This source is associated with a set of detectors arranged in line in the plane in order that each of them receives a well-defined part of the beam. In this system, the source-detector system scans in succession sections by plane parallel to the above mentioned plane of the body by rotation and the body itself by successive displacements perpendicularly to the plane, so that scanning is a unidimensional operation. On the other hand, the Compton effect produces substantial blurring in the images obtained.

The object of the invention is an apparatus of this latter type in which the blur due to the Compton effect, is very largely eliminated.

The device in accordance with the invention comprises an X-ray source, means capable of concentrating the beam emitted, in a plane, and a system of detectors arranged in said plane, and each capable of picking up a well-defined portion of the beam. It is characterized essentially in that each detector is associated with at least one detector located outside the plane of the beam and consequently not receiving direct radiation from the source, and with electrical circuits for producing a linear combination of the electrical signals furnished by the detector and the associated detector.

The invention will be better understood from a consideration of the following description by reference to the attached drawings in which.

Figure 4:
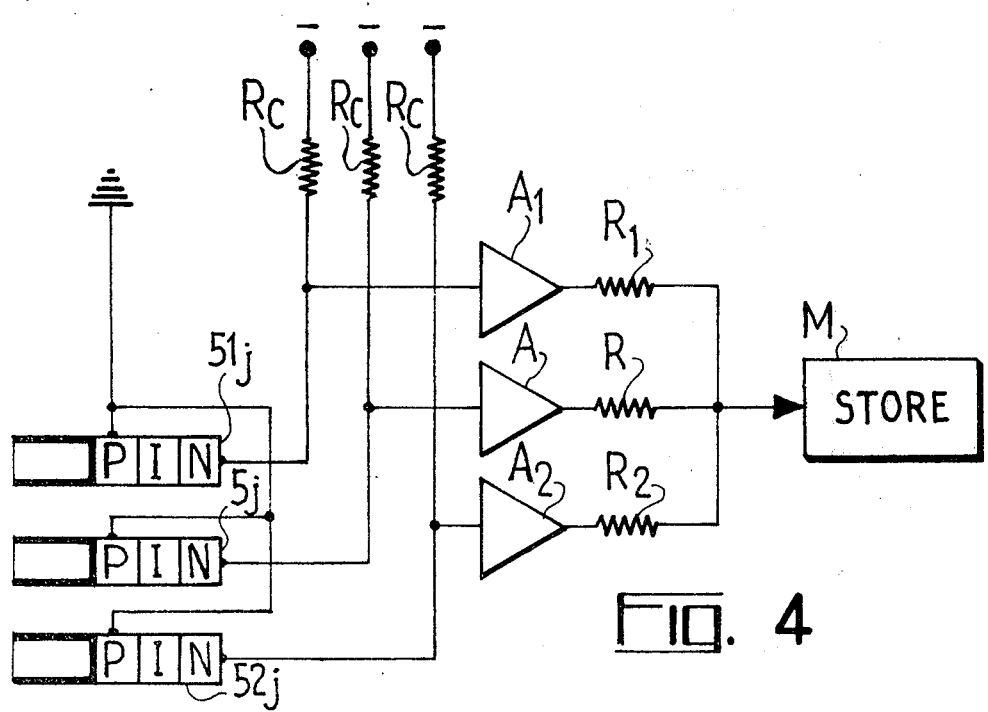
Figure 5:
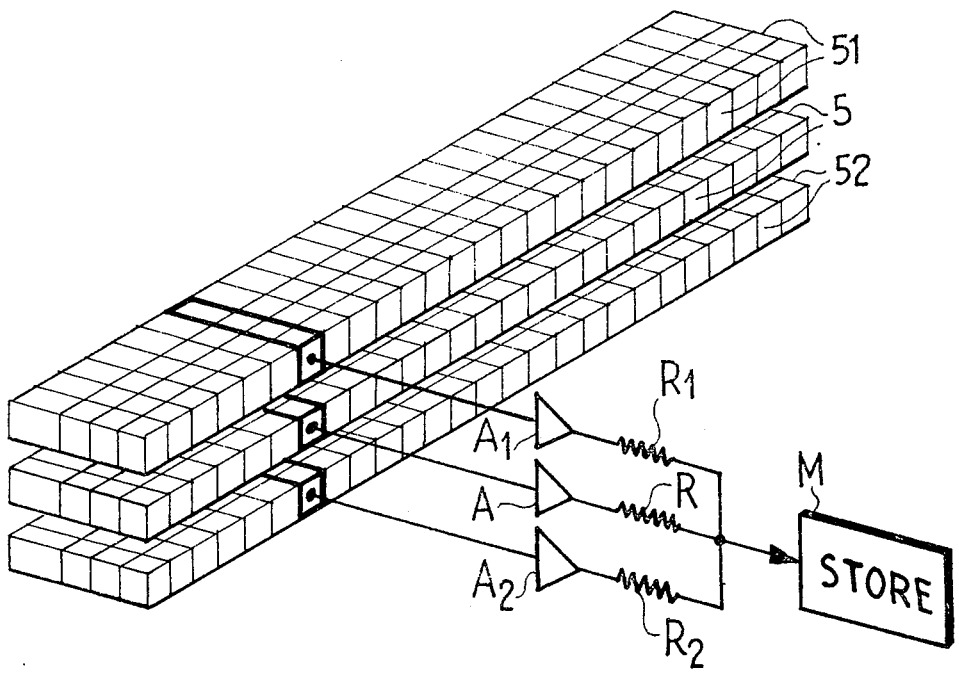

FIGS. 4 and 5 respectively illustrate in section and in perspective, a first embodiment of an electrical circuit for producing an electrical signal from an information element supplied by the X-rays.

Figure 6:
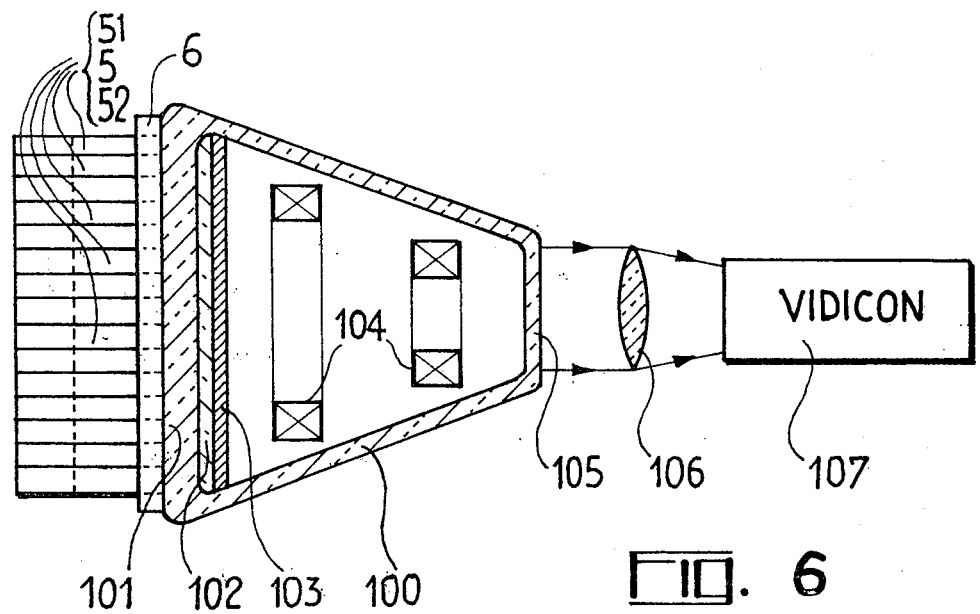

FIG. 6 illustrates in section a second example of a circuit intended for the same application.

Figure 7:
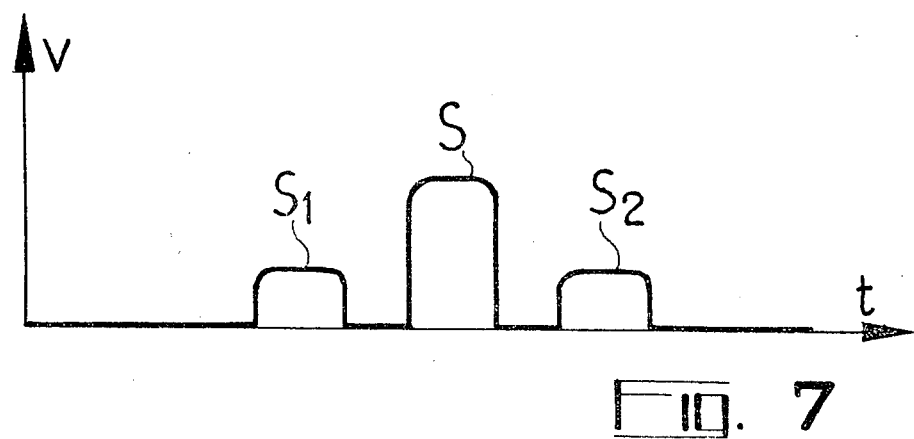

FIG. 7 illustrates the signal obtained at the output of the device shown in FIG. 5.

Figure 8:
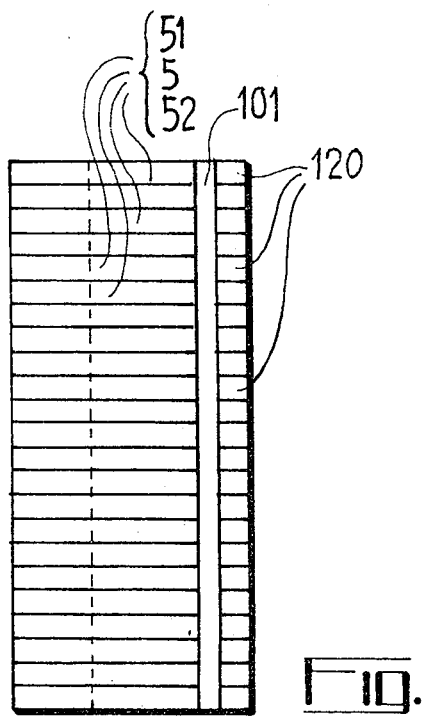

FIG. 8 schematically illustrates, in longitudinal section, a third example.

In all the figures, similar references indicate similar elements.

Figure 1:
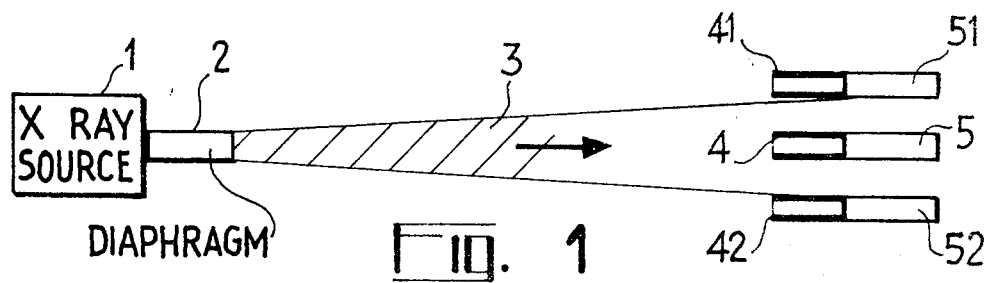
FIGS. 1 and 2 illustrate a longitudinal section and a cross section respectively, of the schematic diagram of the device in accordance with the invention.
Figure 2:
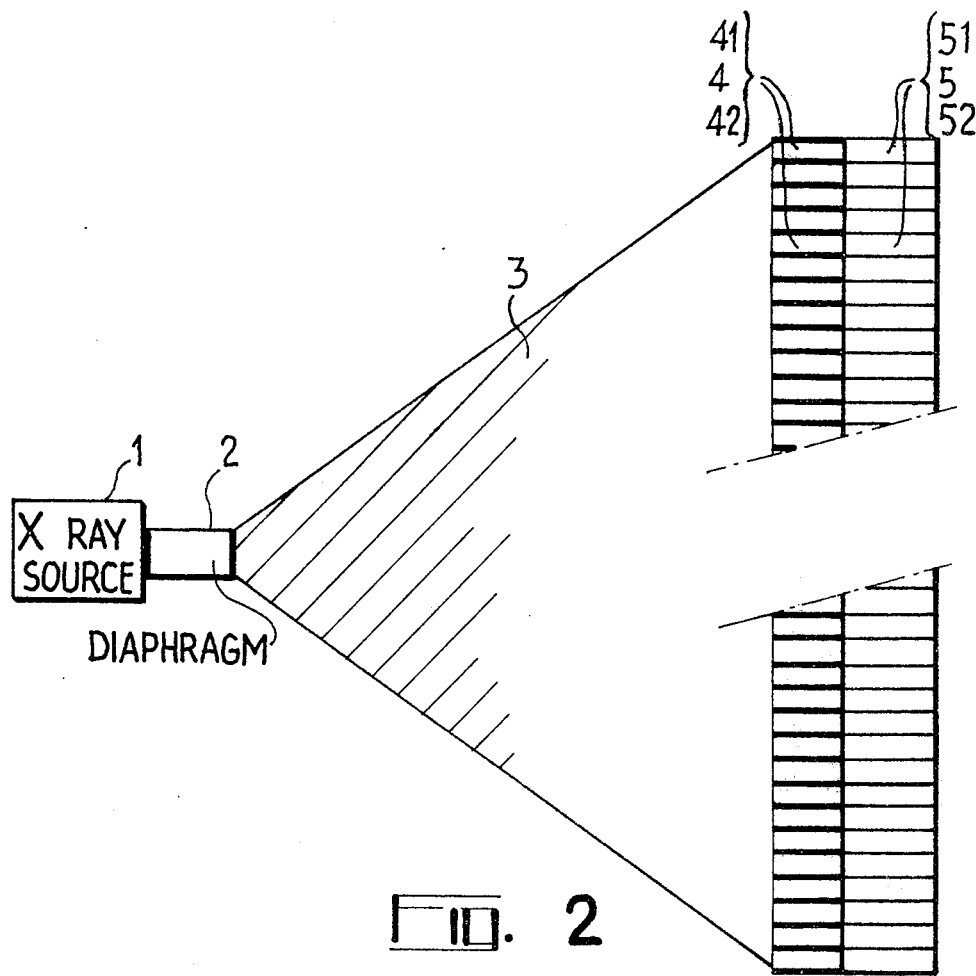
Figure 3:
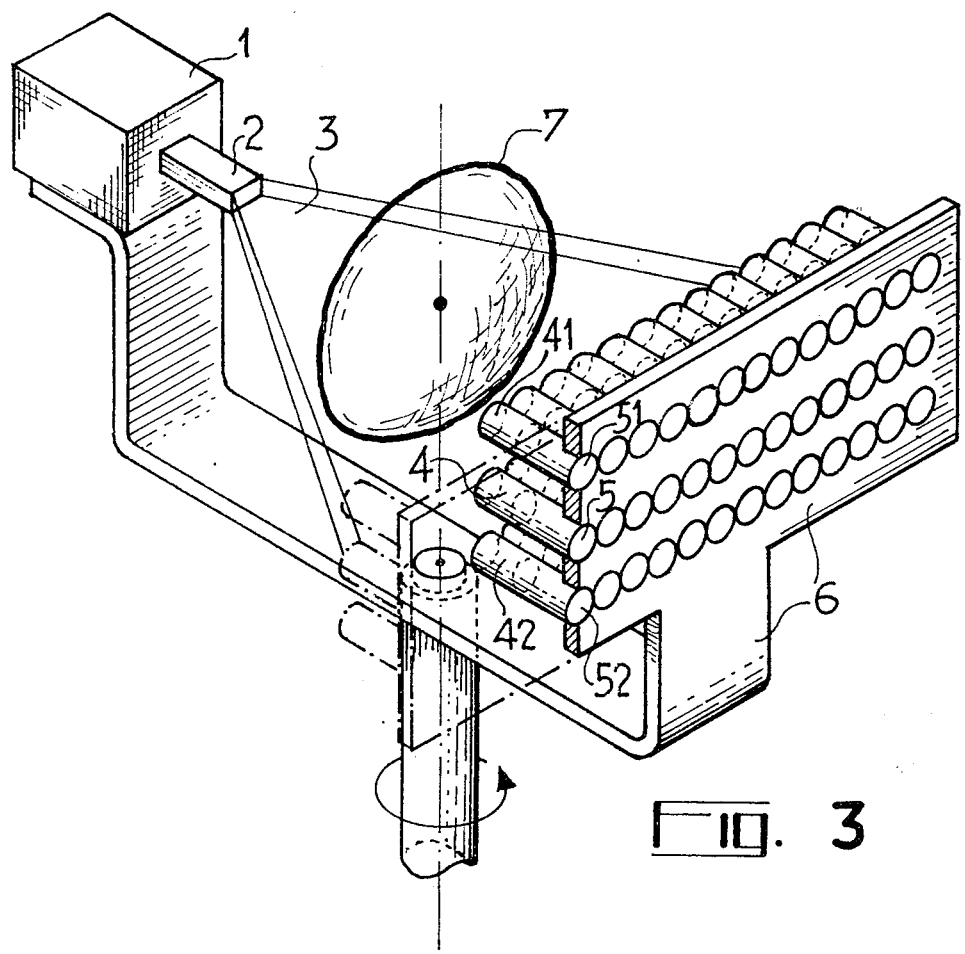
FIG. 3 illustrates the same diagram in perspective.

The device in accordance with the invention comprises an X-ray source 1 arranged behind a diaphragm 2. This source directs a substantially flat X-ray beam 3, onto a set of receptors 5. These receptors are provided with diaphragms 4 enabling each of them to receive a portion of the beam. The set of receptors as well as the source, are carried by the same frame 6 and held together, the source always displacing at the same time as the receptors, as FIGS. 1, 2 and 3 show.

Associated with each receptor 5, in accordance with the invention, there is a receptor 51 with a diaphragm 41 preventing it from receiving any direct radiation from the X-ray source. Preferentially, a second set 52, equipped with diaphragms 42, will be disposed symmetrically in relation to the set 41.

Operation is as follows:

Each receptor element 5 receives an X-ray intensity which corresponds to the absorptive power of the particular portion of a body 7 arranged in the trajectory of the X-rays, the power being picked up by the receptor 5 through its diaphragm.

However, it also receives photons scattered by other portions of the body being analysed, due to the scatter or diffusion effect known as the Compton effect.

In other words, the receptor 5 will receive a light beam whose intensity can be expressed as follows:

$$P_i + D_i$$

$P_i$ being the intensity of the elementary beam at exit from the body being analysed and $D_i$ the energy due to the Compton effect and deriving from the neighbouring beams. However, this latter energy depends essentially upon that portion of the body which has been traversed and consequently there is no means of calculating it if only $P_i$ is known.

It is in order to eliminate this Compton effect, that in accordance with the invention at least one and preferably two auxiliary receptors are provided, associated with each main receptor and, due to the presence of their diaphragms, receiving purely the radiation which is due to the Compton effect.

These two receptors simply receive radiation intensities which, in accordance with the laws of probability, are close to $D_i$.

The invention therefore consists in translating into terms of electrical signals, the radiations received by each doublet or triplet of receptors, and in performing upon these signals the operation:

$$C_i - \left( \frac{D_i}{n_1} - \frac{D_i}{n_2} \right)$$

where $n_1$ and $n_2$ are adjusted to give the best possible correction, and are close to 2.

It will be self-evident that other linear relationships are conceivable and that even a single auxiliary receptor could be used.

In FIGS. 4 and 5, the receptors $5_j$, $51_j$, and $52_j$ ($j = 1 \ldots n$) are PIN-type photodiodes of silicon, the intrinsic part of which is lithium-doped; these diodes have their P regions, for example, earthed, their N regions being connected across a load resistor $R_c$ to the + pole of a common supply source, with the consequence that they are reverse-biased. These diodes behave, vis-a-vis X-rays, as photodiodes and the currents which they produce are function of the intensity of the received X-ray radiation. The output voltage picked off across the terminals of the load resistor, is connected to the input of an operational amplifier A, $A_1$ and $A_2$, for the respective receptors $5_j$, $51_j$, or $52_j$.

The output voltages are applied to three resistors R, $R_1$ and $R_2$ which are designed to produce a linear combination of the three currents flowing through them, or in other words:

$$i - \left(\frac{i_1}{n_1} + \frac{i_2}{n_2}\right)$$

in the example under consideration.

When analysis has been completed, these currents are stored in a store M and can be utilised in a data-processing system. In other words, by displacement of the system in relation to the body being examined, it is possible to divide the latter up into meshes and to determine by calculation the absorbing power of each mesh, as those skilled in the art will be aware.

Other devices are conceivable.

FIG. 6, in plan, views the triple set of receptors 5, 51, 52 and the associated diaphragms. The system is deposited upon one wall 101 of a vacuum tight envelope 100. On said wall there are successively deposited: a photo-scintillation layer 102 opposite the receptor set and a photo-cathode layer 103. An electron-optical system 104 directs the electrons emitted by the photo-cathode onto the fluorescent screen 105 located opposite the wall 101 and constituting the opposite wall of the the envelope.

The envelope 1 has an optical axis on which there is centered an optical lens 106 projecting the image of the screen onto the target of a vidicon tube 107.

The operation of this system is as follows:

The photo-cathode, at each of its elementary areas, emits an electron current which is proportional to the luminous intensity emitted by the associated part of the photo-scintillation arrangement. This luminous intensity is proportional to the quanity of X-rays received by the receptor located opposite.

An image of the system is produced by the screen 105. This image is converted onto a charge image on the target of the vidicon 107. This target is scanned line by line, scanning taking place perpendicularly to the plane of section. With each line-scan, the amplitude of the three signals is proportional to the intensity of the X-rays received by each of the three receptors forming a triplet. These signals have been shown in FIG. 7.

In this figure, there can be seen the main signal S and the two signals $s_1$ and $s_2$ which are due to the Compton effect. The three signals have the same duration but their amplitudes are the electrical translation of the X-ray illumination of each receptor and the associated receptors. These signals are processed as before.

A third solution has been shown in FIG. 8. In this device, photo-scintillation layer 101 is directly deposited upon the set of receptors and with each receptor there is associated an ordinary photodiode 120. This directly produces an electrical signal which is exploited in the manner indicated in FIG. 4.

What I claim is:

1. A radiography apparatus comprising an X-ray source, a collimator system for concentrating the emitted rays in a flat beam, and principal receptors connected to said source and arranged in the plane in order each to receive a predetermined portion of the beam, the set of principal receptors receiving substantially the whole of the beam, and associated with each principal receptor at least one auxiliary receptor, means for shielding said auxiliary receptor from the direct rays emitted by the source so that it only receives the radiation portions emitted as a consequence of the Compton effect, electrical circuits being provided in order to effect a linear combination of the amplitudes of the signals received respectively by the receptor and the auxiliary receptor.

2. An apparatus as claimed in claim 1, wherein a second auxiliary receptor is associated with each receptor, each set of receptors and auxiliary receptors being aligned on a straight line perpendicular to the plane of the beam, the detector being arranged between the two auxiliary detectors and electrical circuits being provided in order to form a linear combination of the signals emitted by the three receptors.

3. An apparatus as claimed in claim 2, wherein a diaphragm is associated with each receptor, the diaphragm of the principal receptor being arranged in order to receive a predetermined portion of the beam being emitted by the source, and the diaphragms of the auxiliary receptors being designed in order to prevent any direct transmission of the x-rays emitted by the source to said auxiliary receptors.

4. An apparatus as claimed in claim 3, wherein the receptors are constituted by reverse-biased X-ray sensitive photodiodes.

5. An apparatus as claimed in claim 4, wherein the photodiodes are made of silicon, the diodes being of P.I.N. type and the I region being lithium-doped.

6. An apparatus as claimed in claim 3, wherein a scintillator is associated with each receptor, a device being provided in order to translate into an electrical signal the amplitude of the light signal emitted by each scintillator.

7. An apparatus as claimed in claim 6, wherein said device comprises a photo-diode associated with each receptor.

8. An apparatus as claimed in claim 6, wherein said device comprises a vacuum tight enclosure, a photo-cathode arranged beside the scintillator, an electron-optical system to form upon a fluorescent screen the image of the scintillator, and a lens in order to form upon the target of a vidicon an electrical charge image of said image produced on said screen.

* * * * *